United States Patent [19]

Cobia et al.

[11] Plant 4,199

[45] Jan. 24, 1978

[54] MILKWEED PLANT FAMILY

[75] Inventors: Barnell L. Cobia, Winter Garden; Stephen H. Griffith, Apopka, both of Fla.

[73] Assignee: B. L. Cobia, Inc., Winter Garden, Fla.

[21] Appl. No.: 760,351

[22] Filed: Jan. 18, 1977

[51] Int. Cl.[2] ..... A01H 5/00

[52] U.S. Cl. ..... Plt./88

[58] Field of Search ..... Plt./88

*Primary Examiner*—Robert E. Bagwill

*Attorney, Agent, or Firm*—Roger L. Martin

[57] ABSTRACT

A new plant variety is distinguishable from specimens of the *Hoya Carnosa* Krinkle 8 variety by a predominance of variegated leaf blades which at the upper epidermal side have a solid green center field and an albino marginal area which is frequently discontinuous, and leaf petioles which in color are dominated by greenish yellow, yellow green, purplish pink, reddish purple, purplish red, pink and/or red hues.

1 Drawing Figure

1

The invention relates to a new and distinct plant variety of the milkweed (Asclepiadaceae) family which has been developed from a mutation that appeared on a plant specimen of the *Hoya Carnosa* Krinkle 8 variety.

A principal objective of the invention has been to develop a healthy robust appearing new plant variety for the foliage plant market and which is related to the *Hoya Carnosa* Krinkle 8 variety and distinguishable from it and other related varieties that are currently being offered in the market place.

The new variety has been asexually reproduced in a nursery at Winter Garden, Fla., by the propagation of stem cuttings taken from the mutation. Through successive propagations, the new variety has been found to be distinguishable from its antecedents and related varieties known to the inventors by a growth habit which is comparable to that of the *Hoya Carnosa* Krinkle 8 variety but which is characterized by the following principally distinguishing characteristics:

1. A predominance of variegated leaf blades which at the upper epidermal side have a solid green center field and an albino marginal area which is frequently discontinuous in the specimen, and 2. Leaf petioles which in color are dominated by greenish yellow, yellow green, purplish pink, reddish purple, purplish red, pink and/or red hues.

The accompanying drawings serve by color photographic means to illustrate the new variety and wherein one sheet of drawings shows a potted plant specimen of the new variety together with a close-up photo showing the variegated foliage characteristics, a second sheet of the drawings illustrates an infloresence and a third sheet contains photographs further illustrating the inflorescence of the new variety.

The following is a detailed description of the new variety and is based on observations made during the months of July and August of well fertilized specimens which were grown in the central Florida area under 85% shaded nursery conditions and wherein temperatures ranged from about 60° F. to about 85° F. during the winter months and from about 75° F. to about 95° F. during the summer months.

Except where general terms of ordinary dictionary significance are obviously used, color terminology and color designations reported herein are in accord with the ISCC-NBS method of designating colors as described in the U.S. Department of Commerce, National

2

Bureau of Standards, Circular 553, entitled "The ISCC-NBS Method of Designating Colors and a Dictionary of Color Names" with the color designations having been derived through interpretation of Munsell Color Notations obtained by comparing specimens with color specimens in the current Neighboring Hues Edition of the Munsell Book of Color, published by Munsell Color Company, Inc., of Baltimore, Md., and to which the reported color notations (Munsell Hue/Munsell Value/Munsell Chroma) are referenced.

PLANT DESCRIPTION

Name: *Hoya Carnosa* 'Krinkle 8 Variegata'

Parentage: *Hoya Carnosa* 'Krinkle 8'

Classification:

*Botanic.*—(Asclepiadaceae) milkweed family.

*Commercial.*—Foliage Plant.

*Form.*—Semisucculent, tropical, twining vine type perennial evergreen with some branching.

Stems:

*General.*—Caulescent, fleshy, herbaceous.

*Texture.*—Moderate pubescent during immaturity and with age becoming glabrous and ultimately covered with thick waxy scale.

*Size.*—Diameter: Usually between 2.5 and 5 mm. at maturity. Internode length: Usually between 15 and 45 mm. and usually somewhat shorter near the root end of the stem.

*Color.*—Commonly varies between specimens and within a specimen. Commonly grayish reddish brown (2.5 YR 4/2) (2.5 YR 3/2), grayish brown (5 YR 4/2) (5 YR 3/2) (7.5 YR 4/2) (7.5 YR 3/2), browish gray (near 5 YR 3/1) (near 10 YR 3/1), grayish yellowish brown (10 YR 4/2), dark grayish yellowish brown (10 YR 3/2), moderate olive brown (2.5 Y 4/2) (2.5 Y 3/2), light olive (near 7.5 Y 5/4) (near 10 Y 5/4), moderate olive (5 Y 4/4) (7.5 Y 4/4) (10 Y 4/4), grayish olive (7.5 Y 4/2) (near 7.5 Y 3/2) (near 10 Y 4/2), moderate olive green (2.5 GY 4/4), grayish olive green (2.5 GY 4/2) and/or moderate yellow green (2.5 GY 5/6) 2.5 GY 5/4) (5 GY 5/6) (5 GY 5/4).

Leaves:

*General.*—Simple, extipulate.

*Arrangement.*—Opposite.

*Margins.*—Entire.

*Venation.*—Pinnate.

*Shape.*—General: Ovate with elliptical tendency and commonly folding along the longitudinal axis with the lateral blade edges curling undulately toward adaxial surface. Leaf apices: Acute with acuminate tendency. Leaf bases: Cordate.

*Petioles.*—General: Herbaceous, fleshy. Texture: Slightly pubescent and with age becoming glabrous and ultimately covered with moderately thick waxy scale. Size: Diameter — Usually between 2 and 5 mm. at maturity. Length — Usually between 7 and 25 mm. at maturity. Color: Dominated by greenish yellow, yellow green, purplish pink, reddish purple, purplish red, pink and/or red hues. Commonly grayish greenish yellow (10 Y 7/4), moderate yellow green (2.5 GY 7/6) (2.5 GY 7/4) (2.5 GY 6/6) (2.5 GY 6/4) (2.5 GY 5/6) (2.5 GY 5/4) (5 GY 7/6) (5 GY 7/4) (5 GY 6/6) (5 GY 6/4) (5 GY 5/6) (5GY 5/4) (near 7.5 GY 5/6), pale purplish pink (near 5 RP 8/4) (near 7.5 RP 8/4), moderate purplish pink (near 2.5 RP 7/6) (near 5 RP 7/6) (near 7.5 RP 7/6), grayish purplish pink (2.5 RP 7/4) (5 RP 7/4) (7.5 RP 7/4), dark purplish pink (5 RP 6/6) (7.5 RP 6/6), pale reddish purple (2.5 RP 6/4), light reddish purple (2.5 RP 6/6 ), light grayish purplish red (5 RP 6/4) (7.5 RP 6/4) (10 RP 6/4), grayish purplish red (near 5 RP 5/4) (near 7.5 RP 5/4) (near 10 RP 5/6) (10 RP 5/4), light pink (near 10 RP 8/4), moderate pink (near 10 RP 8/4) (10 RP 7/4) (near 2.5 R 7/6) (2.5 R 7/4) (5 R 7/4), moderate yellowish pink (near 7.5 R 7/4), dark pink (near 10 RP 6/6), light grayish red (2.5 R 6/4) (5 R 6/4), grayish red (near 2.5 R 5/6) (near 2.5 R 5/4) (near 5 R 5/4), and/or moderate red (2.5 R 5/8) (near 5 R 5/8).

*Leaf blades.*—General: Semisucculent with wrinkled blade caused by depressions or dimples in the surface at the upper epidermal side of the blade and which provide rises in the surface of the lower epidermal side of blade, the depressions or dimples being at opposite sides of the midrib and usually numbering from 6 to 10 in each leaf. Texture: Upper epidermis — Slightly pubescent. Lower epidermis — Moderately pubescent. Size: Length — Usually between 35 and 65 mm. at maturity. Width (maximum) — Usually between 25 and 45 mm. at maturity. Color: Upper epidermal side — A predominance of the mature leaves on mature plants (1 year old) have a solid green center field and an albino marginal area which, in and between blade specimens, varies in the lost content of chlorophyll and in the depth of penetration toward the leaf axis, and which are frequently discontinuous so that the center field color extends to the blade edges at the discontinuities. Commonly strong yellow green (2.5 GY 6/8) (5 GY 6/8), moderate yellow green (2.5 GY 6/6 ) (5 GY 5/6), moderate olive green (7.5 GY 4/6) (7.5 GY 4/4) (7.5 GT 3/4), and/or dark yellowish green (near 10 GT 3/4) (near 2.5 G 3/4) in solid green center field. Commonly brilliant yellow green (2.5 GY 8/8), strong yellow green (2.5 GY 7/8), moderate yellow green (2.5 GY 7/6), yellowish white (near 5 Y 9/2) (near 7.5 Y 9/2), pale yellow (near 5 Y 9/2) (5 Y 9/4) (near 7.5 Y 9/2), light yellow (5 Y 9/6), pale greenish yellow (7.5 Y 9/4) (10 Y 9/4), light greenish yellow (7.5 Y 9/6) (near 7.5 Y 9/8) (near 10 Y 9/8), brilliant greenish yellow (near 7.5 Y 9/8) (near 10 Y 9/8), pale yellow green (10 Y 9/2) and/or translucent white in albino marginal areas of mature specimens. Albino marginal areas in immature leaves are commonly light yellowish pink (near 10 R 8/4) (near 2.5 YR 8/4) (near 5 YR 8/4), moderate yellowish pink (near 10 R 8/4) (near 2.5 YR 8/4) (near 5 YR 8/4), pale orange yellow (near 7.5 YR 8/4) (near 10 YR 9/4) (near 10 YR 9/2) (10 YR 8/4), light orange yellow (near 10 YR 8/6), moderate orange yellow (near 10 YR 8/6), yellowish white (near 10 YR 9/2) (near 2.5 Y 9/2), pale yellow (near 2.5 Y 9/2), light yellow (2.5 Y 8/6) and/or moderate yellow (2.5 Y 8/6). Lower epidermal side — a predominance of the mature leaves (1 year old) have a green center field and an albino marginal area which, in and between blade specimens, varies in the lost content of chlorophyll and in depth of penetration toward the leaf axis, and which are frequently discontinuous so that the center field color extends to the blade edges at the discontinuities, the center fields frequently containing blotches or streaks with albino tendencies. Commonly pale yellow green (2.5 GY 8/2) (5 GY 8/2) (7.5 GY 8/2), light yellow green (2.5 GY 8/6) (2.5 GY 8/4) (5 GY 8/4), and/or moderate yellow green (5 GY 7/4) (7.5 GY 7/4) in center field, and common occurance of greenish white (10 GY 9/1), light greenish gray (10 GY 8/1), and/or very pale green (near 10 GY 8/2) in blotches and streaks. Commonly pale greenish yellow (7.5 Y 9/4) (10 Y 9/4), light greenish yellow (7.5 Y 9/6) (10 Y 9/6), and/or light yellow green (near 2.5 GY 9/4) in mature foliage marginal areas. Marginal areas in immature leaves are commonly yellowish white (near 10 YR 9/2) (near 2.5 Y 9/2) (near 5 Y 9/2) (near 7.5 Y 9/2), pale orange yellow (near 10 YR 9/2), pale yellow (near 2.5 Y 9/2) (near 2.5 Y 8/4) (near 5 Y 9/2) (near 5 Y 8/4) (near 7.5 Y 9/2), grayish yellow (near 2.5 Y 8/4) (near 5 Y 8/4), pale greenish yellow (7.5 Y 9/4) (near 7.5 Y 8/4) (near 10 Y 9/4), light greenish yellow (near 7.5 Y 8/6) (near 10 Y 8/6), moderate greenish yellow (near 7.5 Y 8/6) (near 10 Y 8/6), and/or grayish greenish yellow (near 7.5 Y 8/4).

Inflorescence form: Simple umbel with minute 5-merous bracts and usually between 20 and 45 flowers in a cluster.

Peduncles:

*General.*—Hard, fleshy.

*Texture.*—Pubescent.

*Size.*—Length: Usually between 18 and 35 mm. Diameter (intermediate insertion and pedicel emergence): Usually between 2.3 and 3.8 mm. Shape: Terete.

*Color (pubescence removed).*—Commonly dark grayish red (near 2.5 R 2/2) (2.5 R 3/2) (5 R 3/2) (near 5 R 2/2), blackish red (near 2.5 R 2/2) (near 5 R 2/2), very dark red (near 2.5 R 2/2) (near 5 R 2/2), grayish reddish brown (7.5 R 3/2) (10 R 3/2) (near 2.5 YR 3/2), dark grayish reddish brown (near 7.5 R 2/2) (10 R 2/2) 10 R 2/1) (2.5 YR 2/2), brownish gray (5 YR 3/1), and/or grayish brown (5 YR 3/2).

Pedicels:

*General.*—Fleshy and flexible.

*Texture.*—Slightly pubescent with greater concentration of hairs in distal area.

*Size.*—Length: Usually between 25 and 32 mm. Diameter (intermediate insertion and calyx emergence): Usually between 1.2 and 2 mm.

*Shape.*—Terete and increasing in diameter from emergence to the calyx.

*Color.*—Commonly grayish purplish red (7.5 RP 4/4) (10 RP 5/4) (10 RP 4/4), grayish red (2.5 R 5/4) (2.5 R 4/4) (5 R 5/4) (near 5 R 4/4) (7.5 R 5/4) (7.5 R 4/4), light reddish brown (10 R 5/4) (2.5 YR 6/4) (2.5 YR 5/4), moderate reddish brown (10 R 4/4), light brown (5 YR 6/4) (near 5 YR 5/4) (7.5 YR 6/4), light yellowish brown (near 10 YR 6/4), dark grayish yellow (2.5 Y 6/4) (5 Y 6/4), and/or light olive (5 Y 5/4) (7.5 Y 6/4) with the coloration frequently lightening distally of the emergence.

Flowers:

*General.*—Complete, perfect, actinomorphic and 5-merous type flower with hypogynous perianth and alternate sepal-petal and petal-corona segment arrangements.

*Size.*—Flower radius is usually between 7 and 11 mm. as measured from axis to tip of corolla segment.

*Calyx.*—General: 5-merous with separate, valvate sepals. Sepal texture: Upper epidermis — Glabrous. Lower epidermis — Pubescent. Sepal size (proximal to distal end length): Usually between 2 and 3 mm. Sepal color: Upper epidermal side — Commonly moderate purplish red (7.5 RP 4/8) (10 RP 4/8), grayish purplish red (7.5 RP 4/6) (near 10 RP 4/6) and/or dark purplish red (near 5 RP 3/8) (near 5 RP 3/6) (5 RP 3/4) (7.5 RP 3/6) (near 7.5 RP 3/4) (10 RP 3/6). Lower epidermal side — Commonly grayish purplish red (near 5 RP 5/6) (near 5 RP 5/4) (5 RP 4/4) (7.5 RP 5/6) (7.5 RP 5/4) (7.5 RP 4/6) (7.5 RP 4/4) (10 RP 5/6) (10 RP 4/6) (10 RP 4/4), dark purplish red (5 RP 3/6) (5 RP 3/4) (7.5 RP 3/6) (7.5 RP' 3/4) (10 RP 3/6) (10 RP 3/4) and/or dark reddish purple (2.5 RP 3/4).

*Corolla.*—General: 5-merous, valvate and rotate with interpetal basal fusion for about 1/2 petal length. Petal texture: Upper epidermis — Velutenous. Lower epidermis — Glabrous and waxy. Petal size (proximal to distal end length): Usually between 6 and 10 mm. Petal color: Upper epidermal size — Commonly pale purplish pink (7.5 RP 8/4), light pink (near 10 RP 8/4) (near 2.5 R 8/4), and/or moderate pink (near 10 RP 8/4) (near 2.5 R 8/4) and merging in the proximal area with yellowish white (near 5 Y 9/2) (near 7.5 Y 9/2), pale yellow (near 5 Y 9/2) (near 7.5 Y 9/2), and/or pale yellow green (10 Y 9/2). Lower epidermis — Commonly yellowish white (near 7.5 Y 9/2), pale yellow (near 7.5 Y 9/2), pale yellow green (10 Y 9/2) (2.5 GY 9/2), and/or light yellow green (near 2.5 GY 9/4) in the medial petal area extending along the axis from the proximal end to the distal end and merging laterally and distally with a peripheral area which in color is commonly pale purplish pink (7.5 RP 8/4), light purplish pink (near 10 RP 8/4), moderate purplish pink (near 10 RP 8/4), light pink (near 2.5 R 8/4), and/or moderate pink (near 2.5 R 8/4).

*Corona.*—General: 5-merous, horn like segments which are adnate to stigma and corolla and crested at the proximal ends. Segment texture: Hard, smooth, waxy and glabrous. Segment size: Proximal to distal end length — About 5 mm. Maximum width — About 3 mm. Segment color: Proximal area — Commonly moderate purplish red (7.5 RP 4/8) (near 10 RP 4/10) (10 RP 4/8), dark purplish red (10 RP 3/6) and/or dark red (near 2.5 R 3/6), and merging distally with distal end color. Distal end — Commonly yellowish white (near 5 Y 9/2) (near 7.5 Y 9/2), pale yellow (near 5 Y 9/2) (near 7.5 Y 9/2), and/or pale yellow green (10 Y 9/2) and merging proximally with proximate end color.

*Androecium.*—General: 5-merous pollinium pairs partially enclosed by expanded translucent, perenchymatous translators and attached to stigma through corpuscula located between adjacent segments and with pollinia and translators rising above corpuscula and stigma in converging conical arrangement. Pollinium color: Vivid yellow (5 Y 8/12).

*Gynoecium.*—General: Compound and apocarpous pistil with common stigma. Stigma: General — 5 lobed and waxy. Stigma color — Commonly light yellow (near 5 Y 8/8) (near 5 Y 8/6), moderate yellow (near 5 Y 8/8) (near 5 Y 8/6), strong yellow (near 5 Y 8/8), brilliant yellow (near 5 Y 8/8), light greenish yellow (near 7.5 Y 8/8), moderate greenish yellow (near 7.5 Y 8/8), strong greenish yellow (near 7.5 Y 8/8), and/or brilliant greenish yellow (near 7.5 Y 8/8) and with the apex commonly being moderate purplish red (7.5 RP 4/8) (near 10 RP 4/10) (10 RP 4/8), dark purplish red (10 RP 3/6), and/or dark red (near 2.5 R 3.6). Style: Lacking. Ovary: General — 2 monocarpellate ovullaries with axillary placentation of ovules. Size (length) — About 2 mm. Color — Moderate purplish red (10 RP 4/8).

Growth habit: Vigorous in tropical and semitropical environments with some branching.

The following is a general description of a specimen of the new plant variety which was grown in a nursery at Winter Garden, Fla., from the propagation of a single node cutting having 2 mature leaves.

Age of specimen: 11 months from initial propagation.
Vine length: 272 mm.
Number of nodes: 15.
Number of mature leaves: 22.
Number of immature leaves: 4.
Number of embryonic leaves: 4.

Stem:

*Diameter.*—Ranges from about 4 mm. near the root to about 3 mm. at 4.5 cm. from the tip of the stem.

*Internode distance.*—31 mm. (average).

*Color.*—Grayish reddish brown (2.5 YR4/2) (2.5 YR 3/2), grayish brown (5 YR 4/2) (5 YR 3/2) (near 7.5 YR 4/2) (7.5 YR 3/2), brownish gray (near 5 YR 3/1) (near 10 YR 3/1), and dark grayish yellowish brown (near 10 YR 3/2).

Leaves:

*Petiole (nonembryonic).*—Diameter: 2.6 mm. (average). Length: Ranges from about 10 to 15 mm. with an average length of 12.8 mm. Color: Moderate yellow green (2.5 GY 7/4) (2.5 GY 6/6) (2.5 GY 6/4) (5 GY 7/4) (5 GY 6/6) (5 GY 6/4), grayish purplish pink (7.5 RP 7/4), dark purplish pink (7.5 RP 6/6), light grayish purplish red (7.5 RP 6/4) (10 RP 6/4), moderate pink (10 RP 7/4), and dark pink (near 10 RP 6/6).

*Blades (nonembryonic.)*—Length: Ranges from 41 to 60 mm. with an average of 47 mm. Width: Ranges from 30 to 39 mm. with an average of 34 mm. Color: Upper epidermal side — Moderate olive green (7.5 GY 4/6) (7.5 GY 4/4) in green center field and pale yellow green (10 Y 9/2), yellowish white (near 7.5 Y 9/2), pale yellow (near 7.5 Y 9/2) and white in marginal areas. Lower epidermal side — Pale yellow green (5 GY 8/2) (7.5 GY 8/2), light yellow green (near 5 GY 8/4), moderate yellow green (5 GY 7/4) (7.5 GY 7/4), and very pale green (near 10 GY 8/2) in green center field and pale greenish yellow (7.5 Y 9/4) (10 Y 9/4), light greenish yellow (near 7.5 Y 9/6), and light yellow green (near 2.5 GY 9/4) in marginal areas. Dimples: Ranges from 6 to 10 per blade.

The following is a description of a typical inflorescence that developed on a plant specimen grown in the central Florida area under the conditions indicated heretofore.

Peduncles:

*Age.*—About 6 months.

*Length.*—19 mm.

*Diameter.*—2.8 mm.

*Color.*—Dark grayish red (near 2.5 R 2/2) (2.5 R 3/2) (5 R 3/2) (near 5 R 2/2), blackish red (near 2.5 R 2/2) (near 5 R 2/2), very dark red (near 2.5 R 2/2) (near 5 R 2/2), grayish reddish brown (7.5 R 3/2) (10 R 3/2) (near 2.5 YR 3/2) and dark grayish reddish brown (near 7.5 R 2/2) (10 R 2/2).

Pedicels:

*Number.*—33.

*Length.*—Ranges from 28 to 31 mm. with an average of 29.2 mm.

*Diameter (intermediate insertion and calyx emergence).*—1.6 mm. (average).

*Color.*—Light olive (5 Y 5/4) (7.5 Y 6/4) and dark grayish yellow (5 Y 6/4).

Flowers:

*Number.*—33.

*Radius.*—9 mm. (average).

*Calyx.*—Sepal length: 2.9 mm. (average). Sepal color: Upper epidermal side — Dark purplish red (near 5 RP 3/8) (near 5 RP 3/6) (5 RP 3/4) (7.5 RP 3/6) (near 7.5 RP 3/4) (10 RP 3/6). Lower epidermis — Dark purplish red (10 RP 3/6) (10 RP 3/4) (7.5 RP 3/6) (7.5 RP 3/4) (5 RP 3/6) (5 RP 3/4).

*Corolla.*—Petal size (proximal to distal end length): About 8 mm. (average). Petal color: Upper epidermis — Light pink (near 2.5 R 8/4) and moderate pink (near 2.5 R 8/4) and merging with yellowish white (near 5 Y 9/2), pale yellow (near 5 Y 9/2) and/or pale yellow green (10 Y 9/2) in proximal area. Lower epidermis — Pale yellow green (10 Y 9/2) (2.5 GY 9/2) in median petal areas and light pink (2.5 R 8/4), and moderate pink (2.5 R 8/4) in peripheral areas.

*Corona.*—Segment size: Proximal to distal end length — About 5 mm. Maximum width — About 3 mm. Segment color: Proximal area — Moderate purplish red (7.5 RP 4/8) (10 RP 4/8). Distal area — Yellowish white (near 5 Y 9/2) and pale yellow (near 5 Y 9/2). Pollinium color: Vivid yellow (5 Y 8/12). Stigma color: Light yellow (near 5 Y 8/8), moderate yellow (near 5 Y 8/8), strong yellow (near 5 Y 8/8) and brilliant yellow (near 5 Y 8/8) in proximal area and moderate purplish red (7.5 RP 4/8) at apex. Ovary size: About 2 mm. in length. Ovary color: Moderate purplish red (10 RP 4/8).

We claim

1. The new and distinct variety of the Milkweed Family, substantially as herein shown and described, and which in comparison to the *Hoya Carnosa* 'Krinkle 8' variety is characterized by the following combination of principal distinguishing characteristics:

1. A predominance of variegated leaf blades which at the upper epidermal side have a solid green center field and an albino marginal area which is frequently discontinuous, and
2. Leaf petioles which in color are dominated by greenish yellow, yellow-green, purplish pink, reddish purple, purplish red, pink and/or red hues.

* * * * *

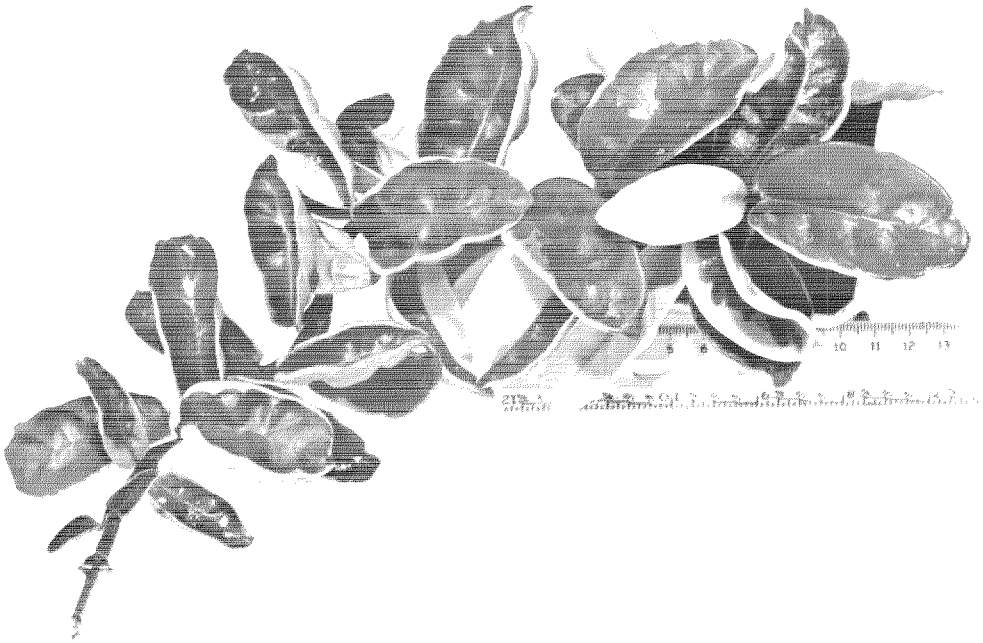
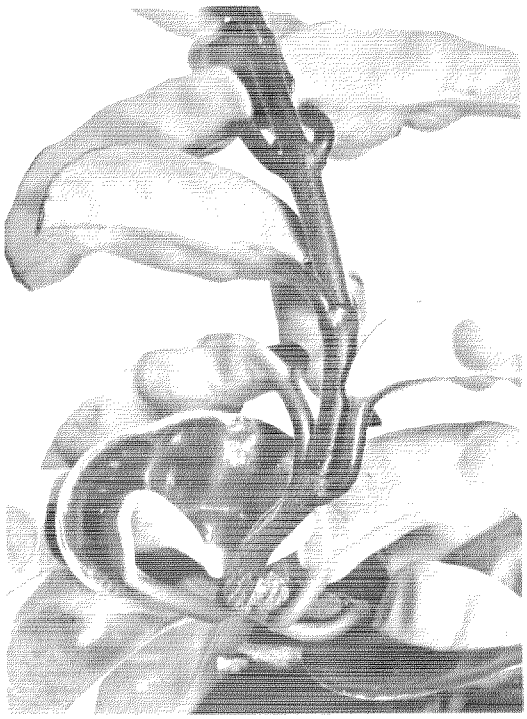

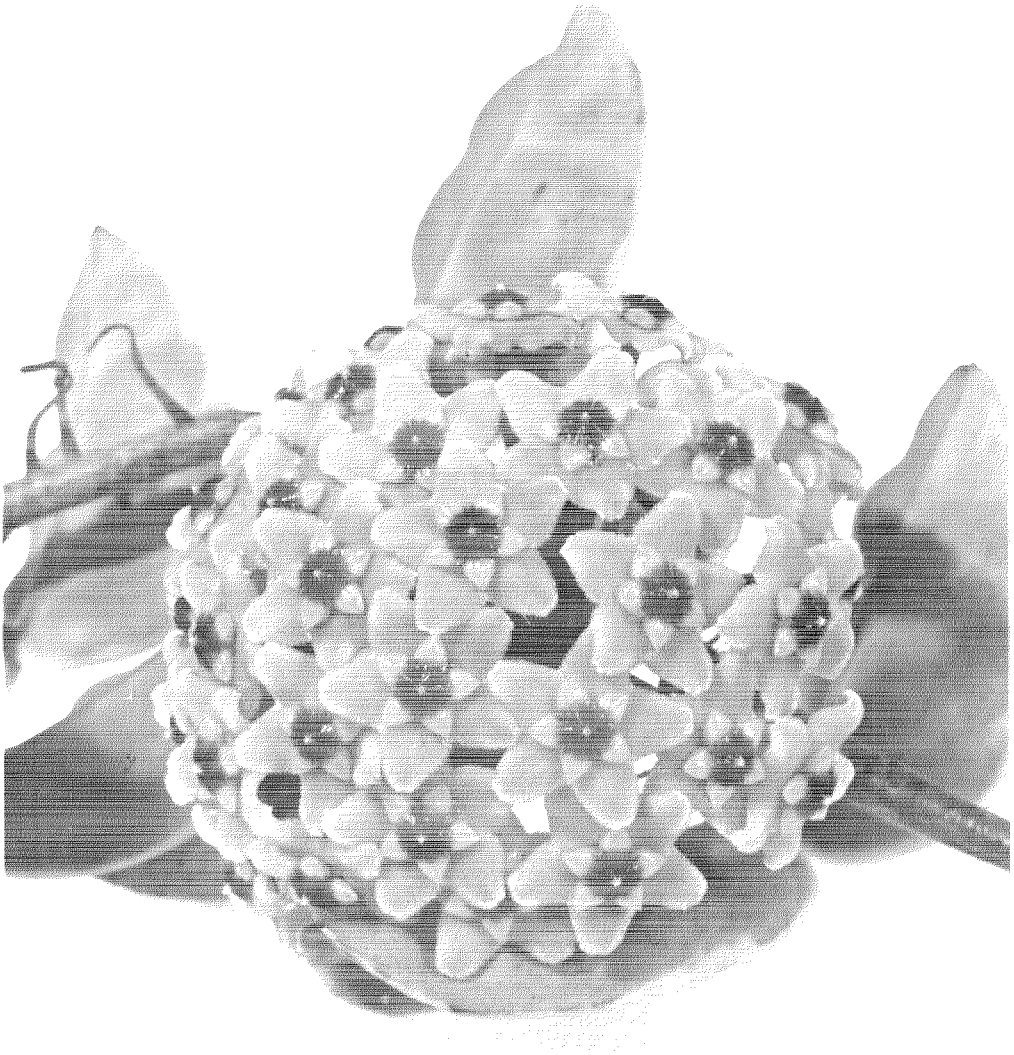

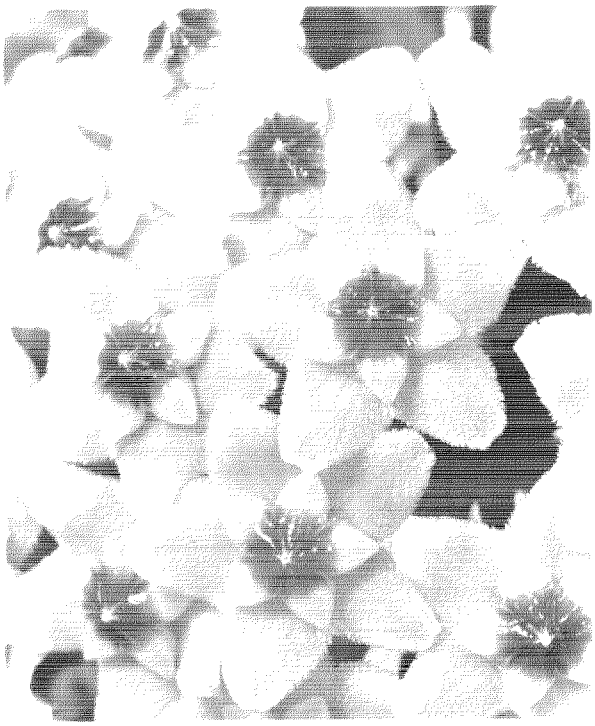
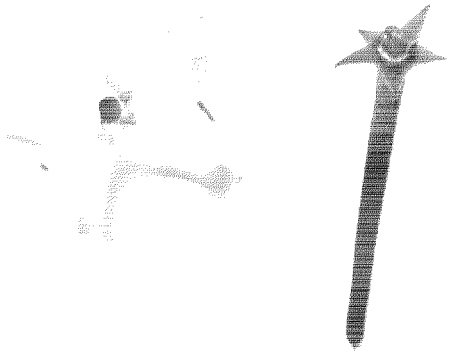

UNITED STATES PATENT AND TRADEMARK OFFICE

CERTIFICATE OF CORRECTION

PATENT NO. : P. 4199

DATED : January 24, 1978

INVENTOR(S) : Barnell L. Cobia and Stephen H. Griffith

It is certified that error appears in the above-identified patent and that said Letters Patent are hereby corrected as shown below:

Col. 2, Line 16, before "Botanic" insert -- A. --; Line 17, before "Commercial" insert -- B. --; Line 18, before "Form" insert -- C. --; Line 21, before "General" insert -- A. --; Line 22, before "Texture" insert -- B. --; Line 25, before "Size" insert -- C. --; Line 25, before "Diameter" insert -- (1) --; Line 26, befor "Internode length" insert -- (2) --; Line 29, before "Color" insert -- D. --; Line 45, before "General" insert -- A. --; Line 46, before "Arrangement" insert -- B. --; Line 47, before "Margins" insert -- C. --; Col. 3, Line 1, before "Venation" insert -- D. --; Line 2, before "Shape" insert -- E. --; Line 2, before "General" insert -- (1) --; Line 5, before "Leaf apices" insert -- (2) --; Line 6, before "Leaf bases" insert -- (3) --; Line 7, before "Petioles" insert -- F. --; Line 7, before "General" insert -- (1) --; Line 7, before "Texture" insert -- (2) --; Line 10, before "Size" insert -- (3) --; Line 10, before "Diameter" insert -- (a) --; Line 11, before "Length" insert -- (b) --; Line 13, before "Color" insert -- (4) --; Line 37, before "Leaf blades" insert -- G. --; Line 37, before "General" insert -- (1) --; Line 44, before "Texture" insert -- (2) --; Line 44, before "Upper epidermis" insert -- (a) --; Line 45, before "Lower epidermis" insert -- (b) --; Line 46, before "Size" insert -- (3) --; Line 46, before "Length" insert -- (a) --; Line 47, before "Width" insert -- (b) --; Line 48, before "Color" insert -- (4) --; Line 49, before "Upper epidermal side" insert -- (a) --; Col. 4, Line 16, before "Lower epidermal side" insert -- (b) --; Line 53, before "General" insert -- A. --; Line 54, before "Texture" insert -- B. --; Line 55, before "Size" insert -- C. --; Line 55, before "Length" insert -- (1) --; Line 56, before "Diameter" insert -- (2) --; Line 58, before "Shape" insert -- (3) --; Line 59, before "Color" insert -- D. --; Col. 5, Line 1, before "General" insert -- A. --; Line 2, before "Texture" insert -- B. --; Line 4, before "Size" insert -- C. --; Line 4, before "Length" insert -- (1) --; Line 5, before "Diameter" insert -- (2) --; Line 7, before "Shape" insert -- D. --; Line 9, before "Color" insert -- E. --; Line 21, before "General" insert

UNITED STATES PATENT AND TRADEMARK OFFICE

CERTIFICATE OF CORRECTION

PATENT NO. : P. 4199

DATED : January 24, 1978

INVENTOR(S) : Barnell L. Cobia and Stephen H. Griffith

It is certified that error appears in the above-identified patent and that said Letters Patent are hereby corrected as shown below:

-- A. --; Line 25, before "Size" insert -- B. --; Line 28, before "Calyx" insert -- C. --; Line 28, before "General" insert -- (1) --; Line 29, before "Sepal texture" insert -- (2) --; Line 29, before "Upper epidermis" insert -- (a) --; Line 30, before "Lower epidermis" insert -- (b) --; Line 30, before "Sepal size" insert -- (3) --; Line 32, before "Sepal color" insert -- (4) --; Line 32, before "Upper epidermal size" insert -- (a) --; Line 37, before "Lower epidermal size" insert -- (b) --; Line 46, before "Corolla" insert -- D. --; Line 46, before "General" insert -- (1) --; Line 48, before "Petal texture" insert -- (2) --; Line 48, before "Upper epidermis" insert -- (a) --; Line 49, before "Lower epidermis" insert -- (b) --; Line 50, before "Petal size" insert -- (3) --; Line 51, before "Petal color" insert -- (4) --; Line 52, before "Upper epidermal side" insert -- (a) --; Line 59, before "Upper epidermis" insert -- (b) --; Col. 6, Line 3, before "Corona" insert -- E. --; Line 3, before "General" insert -- (1) --; Line 5, before "Segment texture" insert -- (2) --; Line 6, before "Segment size" insert -- (3) --; Line 7, before "Proximal to distal end length" insert -- (a) --; Line 8, before "Maximum width" insert -- (b) --; Line 8, before "Segment color" insert -- (4) --; Line 9, before "Proximal area" insert -- (a) --; Line 13, before "Distal end" insert -- (b) --; Line 18, before "Androecium" insert -- F. --; Line 18, before "General" insert -- (1) --; Line 24, before "Pollinium color" insert -- (2) --; Line 26, before "Gynoecium" insert -- G. --; Line 26, before "General" insert -- (1) --; Line 27, before "Stigma" insert -- (2) --; Line 27, before "General" insert -- (a) --; Line 28, before "Stigma color" insert -- (b) --; Line 39, before "Style" insert -- (3) --; Line 39, before "Ovary" insert -- (4) --; Line 39, before "Gen-" insert -- (a) --; Line 42, before "Size" insert -- (b) --; Line 43, before "Color" insert -- (c) --; Line 59, before "Diameter" insert -- (1) --; Line 62, before "Internode distance" insert -- (2) --; Line 63, before "Color" insert -- (3) --; Col. 7, Line 1, before "Petiole" insert -- (1) --; Line 1, before "Diameter" insert -- (a) --; Line 2, before "Length"

UNITED STATES PATENT AND TRADEMARK OFFICE

CERTIFICATE OF CORRECTION

PATENT NO. : P. 4199

DATED : January 24, 1978

INVENTOR(S) : Barnell L. Cobia and Stephen H. Griffith

It is certified that error appears in the above-identified patent and that said Letters Patent are hereby corrected as shown below:

insert -- (b) --; Line 3, before "Color" insert -- (c) --; Line 10, before "Blades" insert -- (2) --; Line 10, before "Length" insert -- (a) --; Line 11, before "Width" insert -- (b) --; Line 13, before "Color" insert -- (c) --; Line 13, before "Upper epidermal side" insert -- (1) --; Line 18, before "Lower epidermal side" insert -- (2) --; Line 25, before "Dimples" insert -- (d) --; Line 34, before "Age" insert -- (1) --; Line 35, before "Length" insert -- (2) --; Line 36, before "Diameter" insert -- (3) --; Line 37, before "Color" insert -- (4) --; Line 45, before "Number" insert -- (1) --; Line 46, before "Length" insert -- (2) --; Line 48, before "Diameter" insert -- (3) --; Col. 8., Line 1, before "Color" insert -- (4) --; Line 4, before "Number" insert -- (1) --; Line 5, before "Radius" insert -- (2) --; Line 6, before "Calyx" insert -- (3) --; Line 6, before "Sepal length" insert -- (a) --; Line 6, before "Sepal color" insert -- (b) --; Line 7, before "Upper epidermal side" insert -- (1) --; Line 10, before "Lower epidermis" insert -- (2) --; Line 13, before "Corolla" insert -- (4) --; Line 13, before "Petal size" insert -- (a) --; Line 14, before "Petal color" insert -- (b) --; Line 14, before "Upper epi-" insert -- (1) --; Line 19, before "Lower epidermis" insert -- (2) --; Line 23, before "Corona" insert -- (5) --; Line 23, before "Segment size" insert -- (a) --; Line 23, before "Proximal to distal end length" insert -- (1) --; Line 24, before "Maximum width" insert -- (2) --; Line 25, before "Segment color" insert -- (b) --; Line 25, before "Proximal area" insert -- (1) --; Line 27, before "Distal area" insert -- (2) --; Line 28, before "Pollinium color"

UNITED STATES PATENT AND TRADEMARK OFFICE

CERTIFICATE OF CORRECTION

PATENT NO. : P.4199

DATED : January 24, 1978

INVENTOR(S) : Barnell L. Cobia and Stephen H. Griffith

It is certified that error appears in the above-identified patent and that said Letters Patent are hereby corrected as shown below:

insert -- (c) --; Line 29, before "Stigma color" insert -- (d) -- Line 33, before "Ovary size" insert -- (e) --; Line 34, before "Ovary color" insert -- (f) --;

Signed and Sealed this

*Twentieth* Day of *November 1979*

[SEAL]

*Attest:*

RUTH C. MASON
*Attesting Officer*

LUTRELLE F. PARKER
*Acting Commissioner of Patents and Trademarks*